United States Patent [19]

Claremon

[11] Patent Number: 4,552,881

[45] Date of Patent: Nov. 12, 1985

[54] SUBSTITUTED AND BRIDGED PYRIDINES USEFUL AS CALCIUM CHANNEL BLOCKER

[75] Inventor: David A. Claremon, Audubon, Pa.

[73] Assignee: Merck & Co., Inc., Rahway, N.J.

[21] Appl. No.: 636,780

[22] Filed: Aug. 1, 1984

[51] Int. Cl.$^4$ .............................. C07D 221/22
[52] U.S. Cl. ........................ 514/295; 544/60; 544/361; 544/126; 546/97
[58] Field of Search .............. 546/97; 544/60, 361; 514/295

[56] References Cited

PUBLICATIONS

Chem. Abstracts, vol. 99, 1983, 71041u.

*Primary Examiner*—Henry R. Jiles
*Assistant Examiner*—J. Richter
*Attorney, Agent, or Firm*—Salvatore C. Mitri; Joseph F. DiPrima; Michael C. Sudol

[57] ABSTRACT

Novel substituted and bridged pyridines useful as calcium channel blockers, pharmaceutical compositions thereof and methods of treatment are disclosed.

10 Claims, No Drawings

SUBSTITUTED AND BRIDGED PYRIDINES USEFUL AS CALCIUM CHANNEL BLOCKER

BACKGROUND OF THE INVENTION

Substituted dihydropyridines are known to be useful for reducing blood pressure, effecting dilation of the coronary vessels, and preventing urospasms. Typical of such substituted dihydropyridines are those disclosed in U.S. Pat. Nos. 3,923,818; 3,905,970; 4,044,141; 4,237,137; and, 4,285,955. The substituted dihydropyridines disclosed in these patents do not include bridged ring structures.

Weller et al., [J. Org. Chem., 48, pp 3.61–7 (1983)] disclose 1'-methylspiro[benzofuran-3(2H), 4'-piperidine] as a substructure of morphine which is an early intermediate in a general synthesis of morphine but not processing exceptional analgesic activity. Weller et al. also teach the preparation of spiro [benzofuran-3(2H), 4'-(1'H)-pyridines] as potential intermediates in a synthesis of morphine but no biological activity of these compounds is reported.

SUMMARY OF THE INVENTION

This invention is directed to novel substituted and bridged pyridines and derivatives thereof and to methods for preparing such compounds. This invention is also directed to pharmaceutical compositions and methods of treatment for cardiovascular disorders in which high cellular concentration of $Ca^{++}$ is a factor.

DETAILED DESCRIPTION OF THE INVENTION

The specific substituted and bridged pyridine compounds of this invention are represented by the following general structural formulae (I) and (II):

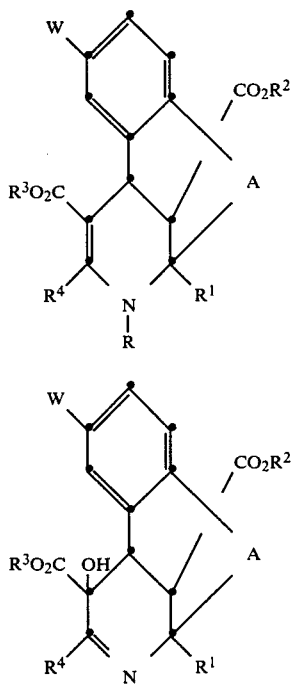

wherein:
A is $>CHCH=CH_2$ or $>CHCH_2CH_3$;

R is hydrogen, $C_{1-C_8}$ alkyl or benzyl;

$R^1$ and $R^4$ independently are $C_{1-C_8}$ alkyl, $C_{2-C_8}$ alkenyl, $C_{3-C_8}$ cycloalkyl, $C_{1-C_8}$ hydroxyalkyl;

$R^2$ and $R^3$ independently are $C_{1-C_8}$ alkyl, $C_{2-C_8}$ alkenyl, $C_{3-C_8}$ cycloalkyl, $C_{1-C_8}$ hydroxyalkyl, $C_{1-C_8}$ dihydroxyalkyl, $C_{2-C_8}$ alkoxyalkyl, $C_{3-C_8}$ alkoxy(alkoxyalkyl), $C_{1-C_8}$ aminoalkyl wherein the amino group is $NR^5R^6$ in which $R^5$ and $R^6$ independently are hydrogen, $C_{1-C_8}$ alkyl, $C_{7-C_{14}}$ phenylalkyl or $R^5$ and $R^6$ together with the N atom form a 5 or 6 membered heterocycle selected from the group consisting of piperidinyl, morpholinyl, thiomorpholinyl, pyrrolidinyl, piperazinyl or $N'-C_1-C_4$-alkylpiperazinyl, or $R^3$ together with $R^4$ is methylene or ethylene; and W is Hydrogen, $C_{1-C_8}$ alkoxy, $C_{1-C_8}$ alkylthio, $C_{1-C_8}$ alkyl S(O), $C_{1-C_8}$ alkyl S(O)$_2$, $CF_3$, cyano or nitro and pharmaceutically acceptable salts thereof.

The preferred compounds of this invention are those represented by the general structural formula (I) wherein:

A is $>CHCH=CH_2$ or $>CHCH_2CH_3$;
R is hydrogen;
$R^1$, $R^2$, $R^3$ and $R^4$ independently are $C_{1-C_8}$ alkyl; and
W is hydrogen, $C_{1-C_8}$ alkoxy, $C_{1-C_8}$ alkylthio, $CF_3$, cyano, or nitro.

The most preferred compounds of this invention are those preferred compounds wherein:
A is $>CHCH=CH_2$; and
W is hydrogen.

The compounds of this invention possess asymmetric centers and thus exist in different isomeric forms. All such forms are included within the scope of this invention. Specifically, the compounds have an asymmetric center at the carbon atom to which the ester moiety, $-CO_2R^2$, is attached. Whenever that ester moiety is below the plane of the piperidine ring (i.e. down) that stereochemical configuration is denoted as the alpha ($\alpha$)-isomer. Similarly, whenever that ester moiety is above the plane of the piperidine ring (i.e. up) that stereochemical configuration is denoted as the beta ($\beta$)-isomer.

Illustrative of the compounds of this invention are the following compounds of the formula (I) which are the $\alpha$-isomer, the $\beta$-isomer or mixtures thereof:

Diethyl 1-ethenyl-1,2,3,6-tetrahydro-2,4-dimethyl-2,6-methano-3-benzazocine-5,11-dicarboxylate [Formula (I) where A is $>CHCH=CH_2$, R is hydrogen, $R^1$ and $R^4$ are methyl, $R^2$ and $R^3$ are ethyl and W is hydrogen] and Diethyl 1-ethyl-1,2,3,6-tetrahydro-2,4-dimethyl-2,6-methano-3-benzazocine-5,11-dicarboxylate [Formula (I) where A is $>CHCH_2CH_3$, R is hydrogen, $R^1$ and $R^4$ are methyl, $R^2$ and $R^3$ are ethyl and W is hydrogen].

Diethyl 1-ethyl-1,2,3,6-tetrahydro-2,4-dimethyl-2,6-methano-3-benzazocine-5,11-dicarboxylate [Formula (I) where A is $CHCH_2CH_3$, R is hydrogen, $R^1$ and $R^4$ are methyl, $R^2$ and $R^3$ are ethyl and W is hydrogen].

The pharmaceutically acceptable salts are those acid addition salts of non-toxic, pharmaceutically acceptable acids and include salts of inorganic acids such as hydrochloric, hydrobromic, hydroiodic, phosphoric, sulfuric, nitric and the like and organic acids such as trifluoroacetic and trichloroacetic, and the like and include acids related to the pharmaceutically acceptable salts listed in Journal of Pharmaceutical Science, 66, 2 (1977) and incorporated herein by reference.

The compounds of this invention are conveniently prepared from known or readily obtainable starting materials utilizing the general synthetic pathway described below:

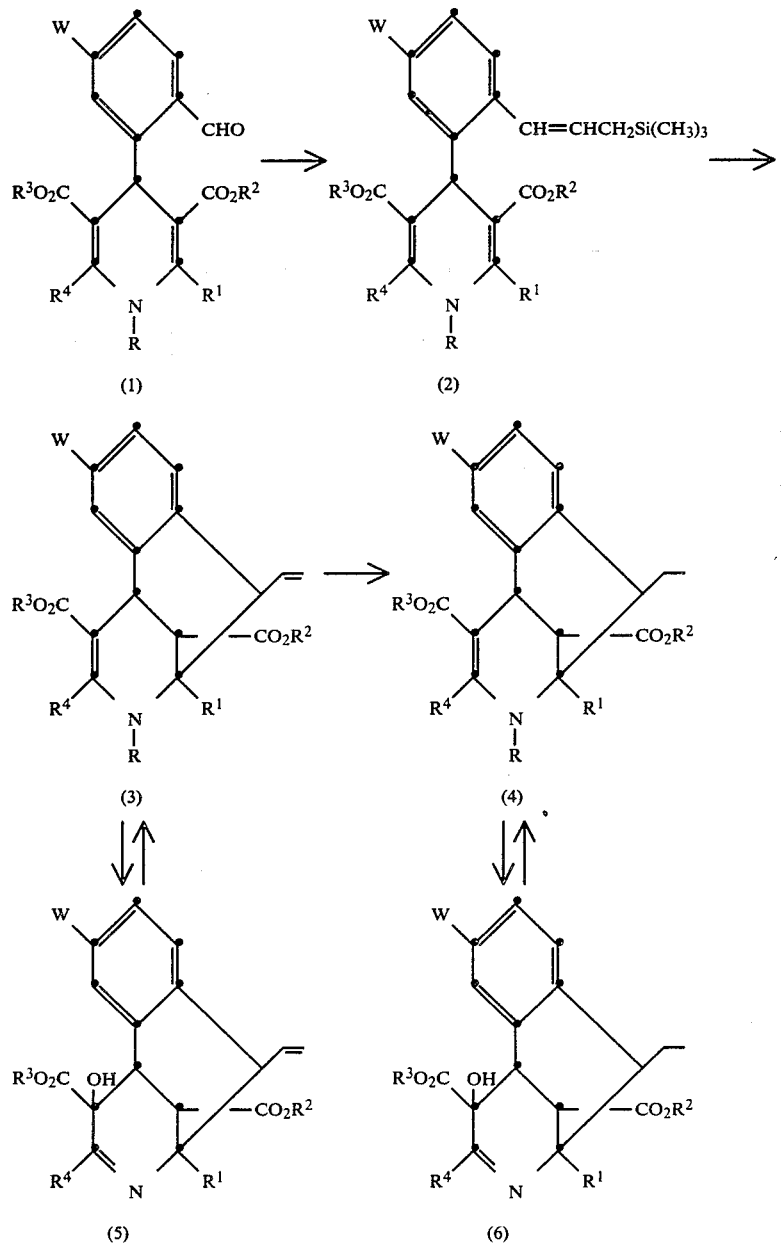

The dihydropyridine compound (1), which is prepared via the Hantzsch Reaction from an appropriately substituted 2-dioxalanylbenzaldehyde and the removal of the dioxalanyl protecting group, is reacted with β-trimethylsilyl ethylidine triphenylphosphorane to give the dihydropyridine compound (2).

The dihydropyridine compound (2) is then treated at −20° to 0° C., preferably 0° C. with (a) between 1.0 and 10 equivalents, preferably 2.0 equivalents of a non-nucleophilic organic base; (b) between 1.5 and 20 equivalents, preferably 10 to 15 equivalents of a Lewis acid and (c) between 50 and 500 equivalents, preferably 100 equivalents of wet silica gel in an inert solvent to yield the Compound (3). Exemplifying the non-nucleophilic organic bases are non-aromatic amines, such as triethylamine, trimethylamine, benzyldimethylamine, dimethylaniline and the like; and aromatic amines, such as pyridine, and the like. Illustrative of the Lewis acids are trimethylsilyl trifluoromethanesulfonate, titanium tetrachloride and tin tetrachloride. Preferably, triethylamine and trimethylsilyl trifluoromethanesulfonate is used in this cyclization reaction. The inert solvents that can be employed in this cyclization reaction include ethers, such as diethyl ether, tetrahydrofuran, dimethoxyethane and the like; chlorinated hydrocarbons, such as methylene chloride, chloroform, dichloroethane and the like; and aromatic hydrocarbons such as benzene and toluene and the like.

The Compound (3) when W is other than nitro may then be hydrogenated under standard conditions to give the Compound (4). The Compound (3) and the Compound (4) may be reacted with an oxidizing agent, such as m-chloroperoxybenzoic acid, to give the Compounds (5) and (6), respectively. Additionally, the Compounds (5) and (6) may be treated with a mild reducing agent, such as aluminum amalgam, to yield the Compounds (3) and (4), respectively.

As indicated above, the compounds of this invention are useful as calcium channel blockers, and thus have broad pharmacological utility in that they exhibit (i) pronounced and long-lasting vasodilating effect accompanied by an energy-sparing effect on cardiac metabolism; (ii) antiarrythmic and antianginal action on cardiac muscle; (iii) vascular spasmolytic action; (iv) antihypertensive action; (v) spasmolytic action on the smooth muscle of the gastrointestinal and urogenital tracts and the cerebrovascular and respiratory system; (vi) useful antihypercholesterolemic and antilipademic action; (vii) protection of the ischemic myocardium; (viii) inhibition of irritable bowel syndrome and esophageal spasm; and, (ix) inhibition of migraine. Some of these compounds are also useful cardiotonic agents.

The representative compounds of the present invention were found to inhibit vascular calcium contraction, reduce cardiac contractile force, inhibit calcium-medicated tracheal contraction, inhibit calcium uptake in pituitary cells, or displace tritiated nitrendipine from membrane.

The Compounds (3) and (5) are also useful as intermediates in the synthesis of other calcium channel blockers. For example, the Compound (5) is treated with an epoxidizing agent, such as m-chloroperoxybenzoic acid or peracetic acid to give compounds of the formula (II) where A is

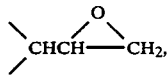

which can be further treated with a mild reducing agent, such as aluminum amalgam to yield compounds of the formula (I) where A is

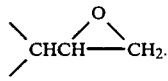

Additionally, the Compound (5) is treated under standard osmylation conditions to afford compounds of the formula (II) where A is

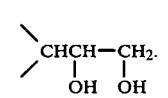

The Compound (3) may be subjected to mild hydroboration followed by oxidation utilizing borane-tetrahydrofuran complex and then trimethylamine-N-oxide to yield compounds of the formula (I) where A is >CHCH$_2$CH$_2$OH which can then be converted under standard conditions to an alkyl ether. Further, the Compound (3) is reacted with hydrogen peroxide, lead (II) acetate and t-butylperoxide to give compounds of the formula (I) where A is

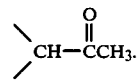

Also, compounds of the formula (I) and (II) where A is either

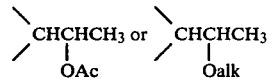

can be prepared from the Compounds (3) and (5) employing phenylselenenyl chloride and the appropriate acetate or alcohol, followed by treatment with tributyltin hydride.

The compounds of the present invention can be administered in any suitable form; e.g. orally, sublingually, transdermally, or parenterally; i.e. intravenously, interperitoneally, etc. Thus, the compounds can be offered in a form (a) for oral administration e.q. as tablets in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for sublingual administration; e.g., nitroglycerine tablets, lactose tablets, and the like, for rapid dissolution or high molecular weight methylcellulose tablets, carboxymethylcellulose tablets, and the like, for slower, time-releasing delivery; or, (c) for parenteral administration e.g. dissolved or dispersed in a suitable liquid carrier or emulsified. The pharmaceutical preparations thus described are made following the conventional techniques of the pharmaceutical chemist as appropriate to the desired end product.

The ratio of active compound to compounding ingredients; i.e., carrier, diluent etc. will vary as the dosage form requires. Whatever form is used, the amount of compound of the present invention administered should be sufficient to achieve the pharmaceutical and/or therapeutic effect desired or required in the patient. Generally, doses of the compounds of the invention of from about 30 to about 3000 mg per day may be used, preferably about 100 to about 1000 mg per day. Dosages may be single or multiple depending on the daily total required and the unit dosage administered. Of course, the dose will vary depending upon the nature and severity of disease, weight of the patient, and other factors which a person skilled in the art will recognize.

It is often advantageous to administer compounds of this invention in combination with angiotensin converting enzyme inhibitors and/or antihypertensives and/or diuretics and/or β-blocking agents. For example, the compounds of this invention can be given in combination with such compounds as enalapril, hydralazine hydrochloride, hydrochlorothiazide, methyldopa, timolol, and the like, as well as admixtures and combinations thereof.

Typically, the individual daily dosages for these combinations can range from about one-fifth of the minimally recommended clinical dosages to the maximum recommended levels for the entities when they are given singly. Naturally, these dose ranges can be adjusted on a unit basis as necessary to permit divided daily dosages and, as noted above, can be varied depending on the nature and severity of the disease, weight of patient, special diets and other factors.

The following Examples are provided to further illustrate the best mode currently known for obtaining the compounds of the invention, but are not to be construed as being limitative of the invention.

EXAMPLE 1

Preparation of Diethyl 1-ethenyl-1,2,3,6-tetrahydro-2,4-dimethyl-2,6-methano-3-benzazocine-5,11-dicarboxylate (a) Diethyl 2,5-dimethyl-4-[2-[1-trimethylsilylpropen-2-yl)]phenyl]-1,4-dihydropyridine-3,5-dicarboxylate (1a)

To a solution of diethyl 2,5-dimethyl-4-(2-formyl-phenyl)-1,4-dihydropyridine-3,5-dicarboxylate (12.6 mmol) in dry tetrahydrofuran (15 ml) was added dropwise at $-78°$ C. a solution of $\beta$-trimethylsilylethylidene triphenylphosphorane[1] (35 mmol) in dry tetrahydrofuran (35 ml). The reaction mixture was allowed to cool to 25° C. and stirred for an additional 16 hours. The reaction mixture was diluted with hexane (150 ml) and filtered through silica gel, which was then washed with ethyl acetate:hexane (1:1, 200 ml). The solvents were removed in vacuo and the residue was purified by flash chromatography on silica gel eluted with ethyl acetate:hexane (1:1) to afford the desired product as a yellow oil.

[1]Fleming et al., Synthesis, p. 446 (1979).

$^1$H NMR (360 MHz, CDCl$_3$) $\delta$=6.02 (dt, 15.0, 9.0 Hz, 1H, $\underline{H}$C-CH$_2$Si)

(b) Diethyl 1-ethenyl-1,2,3,6-tetrahydro-2,4-dimethyl-2,6-methano-3-benzazocine-5,11-dicarboxylate To a solution of Compound 1a (6.24 mmol) in dry methylene chloride (25 ml) at 0° C. under argon was added triethylamine (12.4 mmol) and then trimethylsilyl trifluoromethanesulfonate (74.9 mmol). After stirring for 30 minutes at 0° C., the reaction mixture was cooled to $-15°$ C. and wet silica gel (2.5 g) was added in one portion. After stirring for 15 minutes, the reaction mixture was filtered and silica gel washed with methylene chloride (100 ml). The combined filtrates were extracted with water and saturated aqueous sodium bicarbonate. The organic phase was dried over anhydrous magnesium sulfate and filtered. The filtrate was concentrated in vacuo and the residue purified by flash chromatography eluted with acetone:methylene chloride (25:975) to afford two disastereomers denoted Compounds 1A and 1B, respectively.

Compound 1A
$^1$H NMR (360 MHz, CDCl$_3$) $\delta$=3.94 (bd, J=9.0 Hz,1H, ArC$\underline{H}$CH=CH$_2$).
Compound 1B
$^1$H NMR (360 MHz, CDCl$_3$) $\delta$=3.41 (bd, J=9.0 Hz,1H, ArC$\underline{H}$CH=CH$_2$).

EXAMPLE 2

Preparation of Diethyl 1-ethyl-1,2,3,6-tetrahydro-2,4-dimethyl-2,6-methano-3-benzazocine-5,11-dicarboxylate A solution of the Compound 1B (0.28 mmol) in absolute ethanol (10 ml) was stirred at ambient temperature with 5% palladium on charcoal under a hydrogen atmosphere for 48 hours. The reaction mixture was filtered and the filtrate concentrated in vacuo to yield the desired product as a white solid.

$^1$H NMR (360 MHz, CDCl$_3$) $\delta$=2.55 (m,2H, ArC$\underline{H}$CH$_2$ and C$\underline{H}$CO$_2$).

EXAMPLE 3

Preparation of Diethyl 1-ethenyl-5-hydroxy-1,2-dihydro-2,4-dimethyl-2,6-methano-3-benzazocine-5,11-dicarboxylate A solution of the Compound 1B (0.14 mmol) in methylene chloride (1 ml) was stirred at 25° C. with meta-chloroperoxybenzoic acid (29 mg) for 24 hours. The reaction mixture was diluted with diethyl ether (100 ml), washed with saturated aqueous sodium bicarbonate and brine, dried over anhydrous magnesium sulfate and filtered. The filtrate was concentrated in vacuo and the residue purified by flash chromatography on silica gel eluted with acetone:methylene chloride (1:9) to yield two diastereomers denoted compounds 3A and 3B, respectively.

Compound 3A - white solid.
$^1$H NMR (360 MHz, CDCl$_3$) $\delta$=1.19 (s, 3H, N=CC$\underline{H}_3$) and $\delta$=3.74 (s, 1H, O$\underline{H}$).
Compound 3B - oil
$^1$H NMR (360 MHz, CDCl$_3$) $\delta$=1.92 (s, 3H, N=CC$\underline{H}_3$) and $\delta$=3.84 (s, 1H, O$\underline{H}$).

EXAMPLES 4–8

Utilizing the general procedure of Example 1, the following compounds of the formula (I) are prepared from the appropriate starting material:

| Compound | A | R | R$^1$ | R$^2$ | R$^3$ | R$^4$ | W |
|---|---|---|---|---|---|---|---|
| 4 | CHCH=CH$_2$ | Me | Me | Me | Me | Me | OMe |
| 5 | CHCH=CH$_2$ | —CH$_2$Ph | —CH$_2$CH=CH$_2$ | Me | Me | —CH$_2$CH=CH$_2$ | CN |
| 6 | CHCH=CH$_2$ | H | Me | —CH$_2$OCH$_2$CH$_2$OCH$_3$ | Me | Me | NO$_2$ |
| 7 | CHCH=CH$_2$ | H | Me | —CH$_2$N—CH$_3$<br>\|<br>CH$_2$Ph | Me | Me | CF$_3$ |
| 8 | CHCH=CH$_2$ | H | Me | Me | | —CH$_2$CH$_2$— | SMe |

EXAMPLES 9–13

Utilizing the general procedure of Example 2, the following compounds of the formula (I) are prepared from the appropriate starting material:

| Compound | A | R | R¹ | R² | R³ | R⁴ | W |
|---|---|---|---|---|---|---|---|
| 9 | CHCH₂CH₃ | Me | Me | Me | Me | Me | OMe |
| 10 | CHCH₂CH₃ | —CH₂Ph | Pr | Me | Me | Pr | CN |
| 11 | CHCH₂CH₃ | H | Me | —CH₂OCH₂CH₂OCH₃ | Me | Me | SoMe |
| 12 | CHCH₂CH₃ | H | Me | —CH₂N—CH₃<br>\|<br>CH₂Ph | Me | Me | CF₃ |
| 13 | CHCH₂CH₃ | H | Me | Me | —CH₂CH₂— | | SMe |

EXAMPLES 14–19

Utilizing the general procedure of Example 3, the following compounds of the formula (II) are prepared from the appropriate starting material:

| Compound | A | R¹ | R² | R³ | R⁴ | W |
|---|---|---|---|---|---|---|
| 14 | CHCH₂CH₃ | Me | Et | Et | Me | H |
| 15 | CHCH=CH₂ | Me | CH₂CH₂OH* | Me | Me | OMe |
| 16 | CHCH=CH₂ | —CH₂CH=CH₂ | Me | Me | —CH₂CH=CH₂ | CN |
| 17 | CHCH=CH₂ | Me | —CH₂OCH₂CH₂OCH₃ | Me | Me | NO₂ |
| 18 | CHCH₂CH₃ | Me | —CH₂NCH₃<br>\|<br>CH₂Ph | Me | Me | CF₃ |
| 19 | CHCH₂CH₃ | Me | Me | —CH₂CH₂— | | SO₂Me |

*It should be noted that in the preparation of Compound 15 the hydroxyalkyl moiety is acylated with acetic anhydride prior to cyclization and then deacylated with sodium hydroxide.

EXAMPLE 20

As a specific embodiment of a composition of this invention an active ingredient, such as diethyl 1-ethenyl-1,2,3,6-tetrahydro-2,4-dimethyl-2,6-methano-3-benzazocine-5,11-dicarboxylate, is formulated to yield 5000 compressed tablets, each containing 50 mg of the active ingredient, as follows:

Active Ingredient:250 grams
Starch:70 grams
Dibasic calcium phosphate hydrous:500 grams
Calcium stearate:2.5 grams

What is claimed is:

1. A compound represented by the following general structural formulae (I) and (II):

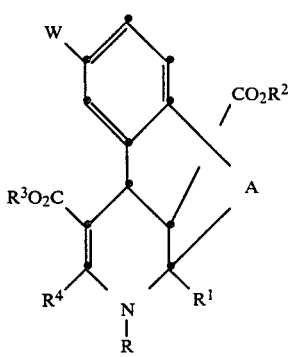

(I)

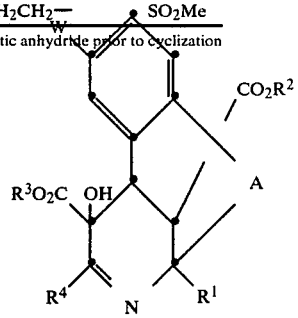

(II)

wherein:
A is >CHCH=CH₂ or >CHCH₂CH₃;
R is hydrogen, $C_{1-C8}$ alkyl or benzyl;
R¹ and R⁴ independently are $C_{1-C8}$ alkyl, $C_{2-C8}$ alkenyl, $C_{3-C8}$ cycloalkyl, $C_{1-C8}$ hydroxyalkyl;
R² and R³ independently are $C_{1-C8}$ alkyl, $C_{2-C8}$ alkenyl, $C_{3-C8}$ cycloalkyl, $C_{1-C8}$ hydroxyalkyl, $C_{1-C8}$ dihydroxyalkyl, $C_{2-C8}$ alkoxyalkyl, $C_{3-C8}$ alkoxy(alkoxyalkyl), $C_{1-C8}$ aminoalkyl wherein the amino group is NR⁵R⁶ in which R⁵ and R⁶ independently are hydrogen, $C_{1-C8}$ alkyl, $C_{7-C14}$ phenylalkyl, together with R⁴ is methylene or ethylene; and
W is hydrogen, $C_{1-C8}$ alkoxy, $C_{1-C8}$ alkylthio, $C_{1-C8}$ alkyl S(O), $C_{1-C8}$ alkyl S(O)₂, CF₃, cyano, nitro, or a pharmaceutically acceptable salt thereof.

2. A compound according to claim 1 represented by the formula (I) wherein:
R is hydrogen;
R¹ and R⁴ independently are $C_{1-C8}$ alkyl;
R² and R³ independently are $C_{1-C8}$ alkyl, $C_{3-C8}$ alkoxy (alkoxyalkyl) or $C_{1-C8}$ aminoalkyl wherein the amino group is NR⁵R⁶ in which R⁵ and R⁶ independently are hydrogen, $C_{1-C8}$ alkyl or $C_{7-C14}$ phenylalkyl; and
W is hydrogen, $C_{1-C8}$ alkoxy, $C_{1-C8}$ alkylthio, CF₃, cyano or nitro.

3. A compound according to claim 2 wherein:

A is >CHCH=CH$_2$; and

W is hydrogen.

4. A compound according to claim 3 which is diethyl 1-ethenyl-1,2,3,6-tetrahydro-2,4-dimethyl-2,6-methano-3-benzazocine-5,11-dicarboxylate.

5. A compound according to claim 2 wherein:

A is >CHCH$_2$CH$_3$; and

W is hydrogen

6. A compound according to claim 5 which is diethyl 1-ethyl-1,2,3,6-tetrahydro-2,4-dimethyl-2,6-methano-3-benzazocine-5,11-dicarboxylate.

7. A compound according to claim 1 which is diethyl 1-ethenyl-5-hydroxy-1,2-dihydro-2,4-dimethyl-2,6-methano-3-benzazocine-5,11-dicarboxylate.

8. A pharmaceutical composition useful in the treatment of cardiovascular disorders in which a high cellular concentration of Ca++ is a factor comprising a nontoxic therapeutically effective amount of a compound according to claim 1 in an admixture with a pharmaceutically acceptable carrier.

9. A method of treatment for cardiovascular disorders in which a high cellular concentration of Ca++ is a factor which comprises administering to a subject in need of such treatment a nontoxic therapeutically effective amount of a compound according to claim 1.

10. A process for the preparation of a compound according to claim 1 of the formula (I) wherein A is >CHCH=CH$_2$ which comprises treating a compound of the following formula:

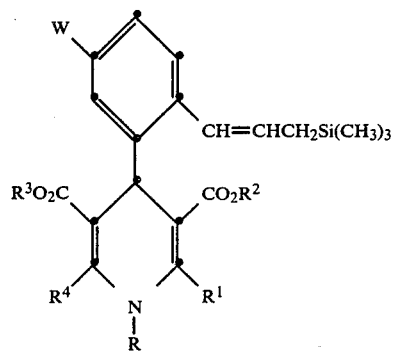

wherein R. R$^1$, R$^2$, R$^3$, R$^4$ and W are described in claim 1, with a non-nucleophilic base, a Lewis acid and silica gel in an inert solvent.

* * * * *